US006806361B1

(12) United States Patent
Kajisa et al.

(10) Patent No.: US 6,806,361 B1
(45) Date of Patent: Oct. 19, 2004

(54) METHODS OF ENHANCING FUNCTIONAL PERFORMANCE OF NUCLEIC ACID ARRAYS

(75) Inventors: Lisa Kajisa, San Jose, CA (US); Glenn McGall, Mountain View, CA (US); Mark Trulson, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/811,143

(22) Filed: Mar. 15, 2001

Related U.S. Application Data

(60) Provisional application No. 60/189,989, filed on Mar. 17, 2000.

(51) Int. Cl.[7] .................. C07H 21/00; C07H 21/04; C12Q 1/68
(52) U.S. Cl. .................. 536/25.3; 536/22.1; 536/23.1; 536/24.3; 435/8
(58) Field of Search .................. 536/25.3, 24.3, 536/23.1, 22.1; 435/6

(56) References Cited

U.S. PATENT DOCUMENTS

| | | |
|---|---|---|
| 5,143,854 A | 9/1992 | Pirrung et al. |
| 5,242,979 A | 9/1993 | Barnum et al. |
| 5,252,743 A | 10/1993 | Barrett et al. |
| 5,288,514 A | 2/1994 | Ellman |
| 5,324,633 A | 6/1994 | Fodor et al. |
| 5,324,663 A | 6/1994 | Lowe |
| 5,384,261 A | 1/1995 | Winkler et al. |
| 5,405,783 A | 4/1995 | Pirrung et al. |
| 5,412,087 A | 5/1995 | McGall et al. |
| 5,424,186 A | 6/1995 | Fodor et al. |
| 5,445,934 A | 8/1995 | Fodor et al. |
| 5,451,683 A | 9/1995 | Barrett et al. |
| 5,482,887 A | 1/1996 | Duinkerken et al. |
| 5,489,678 A | 2/1996 | Fodor et al. |
| 5,491,074 A | 2/1996 | Aldwin et al. |
| 5,510,270 A | 4/1996 | Fodor et al. |
| 5,527,681 A | 6/1996 | Holmes |
| 5,545,531 A | 8/1996 | Rava et al. |
| 5,547,839 A | 8/1996 | Dower et al. |
| 5,550,215 A | 8/1996 | Holmes |
| 5,556,752 A | 9/1996 | Lockhart et al. |
| 5,571,639 A | 11/1996 | Hubbell et al. |
| 5,578,832 A | 11/1996 | Trulson et al. |
| 5,593,839 A | 1/1997 | Hubbell et al. |
| 5,599,695 A | 2/1997 | Pease et al. |
| 5,624,711 A | 4/1997 | Sundberg et al. |
| 5,631,734 A | 5/1997 | Stern et al. |
| 5,658,734 A | 8/1997 | Brock |
| 5,677,195 A | 10/1997 | Winkler et al. |
| 5,677,289 A * | 10/1997 | Torrence et al. .............. 514/74 |
| 5,710,000 A | 1/1998 | Sapolsky et al. |
| 5,744,101 A | 4/1998 | Fodor et al. |
| 5,744,305 A | 4/1998 | Fodor et al. |
| 5,753,788 A | 5/1998 | Fodor et al. |
| 5,770,456 A | 6/1998 | Holmes |
| 5,800,992 A | 9/1998 | Fodor et al. |
| 5,831,070 A | 11/1998 | Pease et al. |
| 5,843,655 A | 12/1998 | McGall |
| 5,856,011 A | 1/1999 | Sogabe |
| 5,919,523 A | 7/1999 | Sundberg et al. |
| 6,022,963 A | 2/2000 | McGall et al. |
| 6,045,996 A | 4/2000 | Cronin et al. |
| 6,147,205 A * | 11/2000 | McGall et al. .......... 536/25.31 |

FOREIGN PATENT DOCUMENTS

| | | |
|---|---|---|
| EP | 7288520 | 8/1996 |
| EP | 742287 | 11/1996 |
| EP | 549107 | 12/1997 |
| EP | 967217 A2 | 12/1999 |
| WO | WO 92/10092 | 6/1992 |
| WO | WO 92/10183 | 6/1992 |
| WO | WO 93/04145 | 3/1993 |
| WO | WO 94/10128 | 5/1994 |
| WO | WO 97/10365 | 3/1997 |
| WO | WO 97/27317 | 7/1997 |
| WO | WO 97/39151 | 10/1997 |
| WO | WO 97/43450 | 11/1997 |
| WO | WO 98/20967 | 5/1998 |
| WO | WO 98/39348 | 9/1998 |
| WO | WO 99/00730 | 1/1999 |
| WO | WO 99/40105 | 2/1999 |
| WO | WO 99/54509 | 10/1999 |
| WO | WO 00/06771 | 2/2000 |
| WO | WO 00/21967 | 4/2000 |
| WO | WO 00/61282 | 10/2000 |

OTHER PUBLICATIONS

Yeung et al, "A general method of optimizing automated DNA synthesis to decrease chemical consumption to less than half", Anal. Biochem. 187:66–75 (1990).*

Synthesis Cycle, Version 2.00 Cycle 10hpaf3, Nov. 2, 1989.*

Sambrook et al, Molecular Cloning: A Laboratory Manual, pp. 1.98–1.99.*

McGall et al., "The Efficiency of Light–Directed Synthesis of DNA Arrays on Glass Substrates" *Journal of the American Chemical Society, 1997*, pp. 5081–5090, vol. 119, No. 22.

Lockhart et al.,"Expression monitoring by hybridization to high–density oligonucleotide arrays" *Nature Biotechnology, 1996*, pp. 1675–1680, vol. 14.

Saizieu et al., "Bacterial transcript imaging by hybridization of total RNA to oligonucleotide arrays" *Nature Biotechnology, 1998*, pp. 45–48, vol. 16.

Chee et al., "Accessing Genetic Information with HighDensity DNA Arrays" *Science, 1996*, pp. 610–614, vol. 274.

(List continued on next page.)

Primary Examiner—Jeffrey Fredman
(74) Attorney, Agent, or Firm—Hamilton, Brook, Smith & Reynolds, P.C.

(57) ABSTRACT

Methods are provided for preparing nucleic acid arrays on a support. In these methods a plurality of nucleic acids are synthesized on the support and the synthesis steps are followed by drying steps in which the array is exposed to a dry atmosphere following the synthesis steps.

17 Claims, 10 Drawing Sheets

OTHER PUBLICATIONS

McGall et al., "High–density oligonucleotide probe arrays" Proc. *SPIE–Int. Soc. Opt. Eng., 2000*, pp. 106–110, vol. 3926 (Advances in Nucleic Acid and Protein Analyses, Manipulation, and Sequencing).

Wallraff et al., "Lithographic techniques for the fabrication of oligonucleotide arrays" *J. Photopolym. Sci. Technol., 2000*, pp. 551–558, Vol 13.

Glazer et al., "High Surface Area Substrates for DNA Arrays" *Mat. Res. Soc. Symp. Proc., 1999*, pp. 371–376, vol. 576.

Fidanza et al., "High–Density Nucleoside Analog Probe Arrays for Enhanced Hybridization" *Nucleosides and Nucleotides, 1999*, pp. 1293–1295, vol. 18.

Hacia et al., "Enhanced High Density Oligonucleotide Array Based Sequence Analysis using Modified Nucleotide Triphosphates" *Nucleic Acids Res., 1998*, pp. 4975–4982, vol. 26.

Pirrung et al., "Proofing of Photolithographic DNA synthesis with 3', 5'—dimethoxybenzolnyloxycarbonyl–protected deoxy–nucleoside phosphoramidites" *J.Org. Chem, 1998*, pp. 241–246, vol. 63.

* cited by examiner

US 6,806,361 B1

METHODS OF ENHANCING FUNCTIONAL PERFORMANCE OF NUCLEIC ACID ARRAYS

CROSS-REFERENCES TO RELATED APPLICATIONS

This application claims the benefit of Ser. No. 60/189,989, filed Mar. 17, 2000, the disclosure of which is incorporated by reference.

STATEMENT AS TO RIGHTS TO INVENTIONS MADE UNDER FEDERALLY SPONSORED RESEARCH AND DEVELOPMENT

Not applicable

BACKGROUND OF THE INVENTION

The present invention relates to improved methods for preparing support-bound nucleic acid arrays.

Substrate-bound nucleic acid arrays, such as the Affymetrix DNA Chip, enable one to test hybridization of a target nucleic acid molecule to many thousands of differently sequenced nucleic acid probes at feature densities greater than about five hundred per 1 $cm^2$. Because hybridization between two nucleic acids is a function of their sequences, analysis of the pattern of hybridization provides information about the sequence of the target molecule. The technology is useful for de novo sequencing and re-sequencing of nucleic acid molecules and also has important diagnostic uses in discriminating genetic variants that may differ in sequence by one or a few nucleotides. For example, substrate-bound nucleic acid arrays are useful for identifying genetic variants of infectious diseases, such as HIV, or genetic diseases, such as cystic fibrosis.

In one version of the substrate-bound nucleic acid array, the target nucleic acid is labeled with a detectable marker, such as a fluorescent molecule. Hybridization between a target and a probe is determined by detecting the fluorescent signal at the various locations on the substrate. The amount of signal is a function of the thermal stability of the hybrids. The thermal stability is, in turn, a function of the sequences of the target-probe pair: AT-rich regions of DNA melt at lower temperatures than GC-rich regions of DNA. This differential in thermal stabilities is the primary determinant of the breadth of DNA melting transitions, even for nucleic acids.

Depending upon the length of the nucleic acid probes, the number of different probes ova substrate, the length of the target nucleic acid, and the degree of hybridization between sequences containing mismatches, among other things, a hybridization assay carried out on a substrate-bound nucleic acid array can generate thousands of data points of different signal strengths that reflect the sequences of the probes to which the target nucleic acid hybridized. This information can require a computer for efficient analysis. The fact of differential fluorescent signal due to differences in thermal stability of hybrids complicates the analysis of hybridization results, especially from combinatorial nucleic acid arrays for de novo sequencing and custom nucleic acid arrays for specific re-sequencing applications. Modifications in custom array designs have contributed to simplifying this problem.

Further complications can arise and lead to variability in diagnostic or sequencing results. For example, degradation of nucleic acid probes, either during the synthesis steps or on standing can lead to variability in assay results. Accordingly, there exists a need for additional methods of nucleic acid array preparation, and the arrays themselves, to provide more robust tools for the skilled researcher. The present invention provides such methods and arrays.

SUMMARY OF THE INVENTION

In one aspect, the present invention provides methods for preparing nucleic acid arrays on a support. In these methods a plurality of nucleic acids are synthesized on the support and the synthesis steps are followed by drying steps in which the array is exposed to a dry atmosphere following the synthesis steps.

In one group of embodiments, each nucleic acid occupies a separate known region of the support, the synthesizing comprising:
  (a) activating a region of the support;
  (b) attaching a nucleotide to a first region, the nucleotide having a masked reactive site linked to a protecting group;
  (c) repeating steps (a) and (b) on other regions of the support whereby each of the other regions has bound thereto another nucleotide comprising a masked reactive site linked to a protecting group, wherein the other nucleotide may be the same or different from that used in step (b);
  (d) removing the protecting group from one of the nucleotides bound to one of the regions of the support to provide a region bearing a nucleotide having an unmasked reactive site;
  (e) binding an additional nucleotide to the nucleotide with an unmasked reactive site;
  (f) repeating steps (d) and (e) on regions of the support until a desired plurality of nucleic acids is synthesized, each nucleic acid occupying separate known regions of the support;
    wherein some or all of the attaching and binding steps are followed by drying steps in which the support is exposed to a dry atmosphere for a period of time sufficient to reduce pitting on the array. Typically, the dry atmosphere is dry air (preferably dry filtered air), nitrogen or argon, or mixtures thereof, and the period of time is at least 30 seconds, although times of 45 seconds or one minute or more can also be used.

In another group of embodiments, the preparing comprises the sequential steps of:
  a) removing a photoremovable protecting group from at least a first area of a surface of a substrate, the substrate comprising immobilized nucleotides on the surface, and the nucleotides capped with a photoremovable protective group, without removing a photoremovable protecting group from at least a second area of the surface;
  b) simultaneously contacting the first area and the second area of the surface with a first nucleotide to couple the first nucleotide to the immobilized nucleotides in the first area, and not in the second area, the first nucleotide capped with a photoremovable protective group;
  c) removing a photoremovable protecting group from at least a part of the first area of the surface and at least a part of the second area;
  d) simultaneously contacting the first area and the second area of the surface with a second nucleotide to couple the second nucleotide to the immobilized nucleotides in at least a part of the first area and at least a part of the second area;
  e) performing additional removing and nucleotide contacting and coupling steps so that a matrix array of at least 100 nucleic acids having different sequences is formed on the support;

with the proviso that the coupling steps further comprise a drying step wherein the solid support is exposed to a dry atmosphere as described above and as further described in detail below.

In another group of embodiments, the nucleoside phosphoramidite monomers used in the invention have the formula:

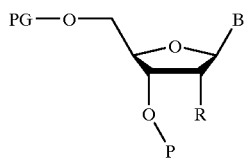

wherein B represents adenine, guanine, thymine, cytosine, uracil or analogs thereof; R is hydrogen, hydroxy, protected hydroxy, halogen or alkoxy; P is a phosphoramidite group; and PG is a photoremovable protected group.

BRIEF DESCRIPTION OF THE DRAWINGS

In FIG. 8, the drying time was 10-seconds. In FIG. 9, a standard drying time of 25 seconds was used. In FIG. 10, a 75-second drying time was used.

DETAILED DESCRIPTION OF THE INVENTION

Definitions

Figure 1:
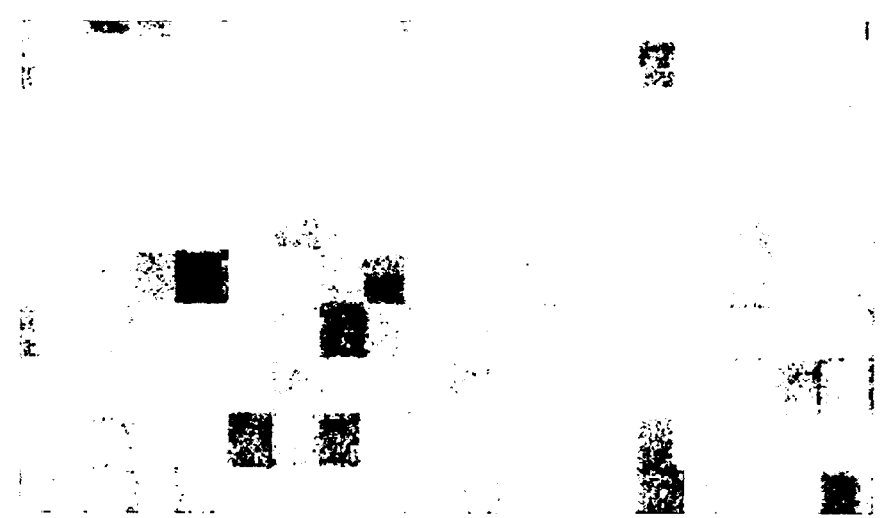
FIG. 1 shows a clean image of a nucleic acid array.

The following definitions are set forth to illustrate and define the meaning and scope of the various terms used to describe the invention herein.

"Nucleic acid library" or "array" is an intentionally created collection of nucleic acids which can be prepared either synthetically or biosynthetically and screened for biological activity in a variety of different formats (e.g., libraries of soluble molecules; and libraries of oligos tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate. The term "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired. "Solid support", "support", and "substrate" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations.

"Predefined region" or "preselected region" refers to a localized area on a solid support which is, was, or is intended to be used for formation of a selected molecule and is otherwise referred to herein in the alternative as a "selected" region, a "known" region, or a "known" location. The predefined or known region may have any convenient shape, e.g., circular, rectangular, elliptical, wedge-shaped, etc. For the sake of brevity herein, "predefined regions" are sometimes referred to simply as "regions." In some embodiments, a predefined or known region and, therefore, the area upon which each distinct compound is synthesized is smaller than about 1 $cm^2$ or less than 1 $mm^2$. Within these regions, the molecule synthesized therein is preferably synthesized in a substantially pure form. In additional embodiments, a known region can be achieved by physically separating the regions (i.e., beads, resins, gels, etc.) into wells, trays, etc. Accordingly, materials (e.g., nucleic acids) can be synthesized or attached to any particular region by any known methods or means.

General

Nucleic acid arrays having single-stranded nucleic acid probes have become powerful research tools for identifying and sequencing new genes. Other arrays of unimolecular double-stranded DNA have been developed which are useful in a variety of screening assays and diagnostic applications (see, for example, U.S. Pat. No. 5,556,752). Still other arrays have been described in which a ligand or probe (a peptide, for example), is held in a conformationally restricted position by two complementary nucleic acids, at least one of which is attached to a support. Common to each of these types of arrays is the presence of a support-bound nucleic acid and the exquisite sensitivity exhibited by the arrays. Unfortunately, the sensitivity of these arrays can be compromised if the nucleic acids are degraded or are not prepared in sufficient quantity on the support.

In order to provide the researcher with arrays of uncompromising quality and reproducible performance, arrays should be prepared using high yield reactions and excluding any component which could negatively impact synthesis yield or the performance of the array.

Figure 2:
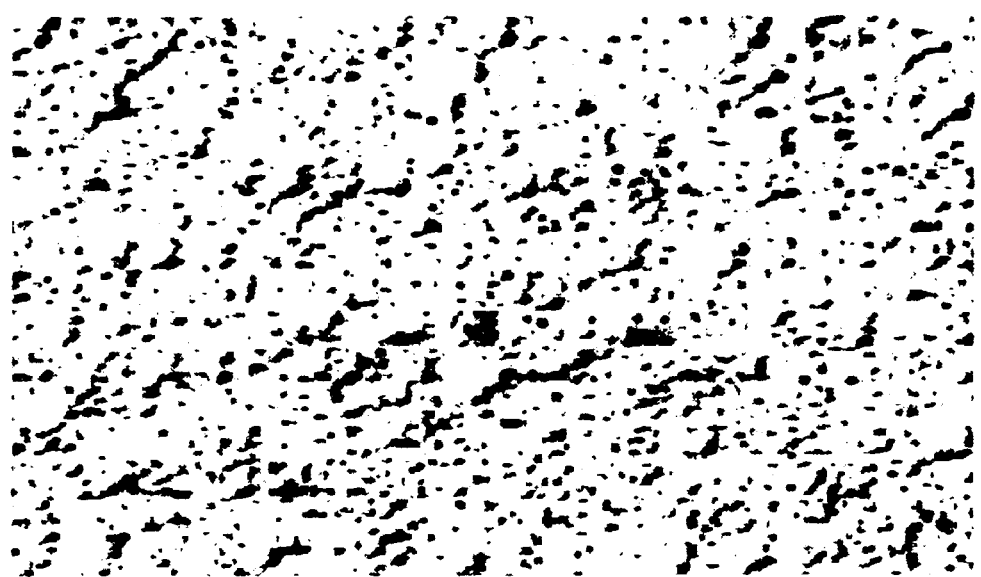
FIG. 2 shows a pitted image of a nucleic acid array taken from the #7 corner of a prepared wafer.

The present invention derives from the discovery that improved arrays can be obtained if the arrays are subjected to supplemental drying at the end of the chemical (or monomer) addition cycles. More particularly, pitting was found to occur in nucleic acids arrays when the support is not-sufficiently dried between chemical coupling steps. FIG. 1 shows a "clean image" array while FIG. 2 shows a "pitted" array. Pitting in this context is apparent as a flurry of irregularly shaped dark spots (about 1–20 microns in size) in scanned images of hybridized arrays. While pitting was generally confined to a portion of the initial wafer, the removal of chips from that portion led to a loss of approximately 20% of manufacturing capacity for that product. Accordingly, the new methods have provided a recovery of the 20% loss. More particularly, when the process was altered to provide for about 30 seconds of supplemental drying (argon purge) following the standard cycle of base addition, pitting was immediately reduced from about 88% of the production wafers to about 0%. Additionally, the supplemental drying procedure did not negatively impact the functional performance.

Embodiments of the Invention

In view of the above discoveries, the present invention provides an improved method of preparing a nucleic acid array on a support. In a general sense, the method comprises synthesizing a plurality of nucleic acids on a support wherein the synthesis steps comprise coupling nucleic acid monomers to a support and drying the array by exposing the support to a dry atmosphere for a period of at least 30 seconds.

More particularly, the arrays are dried following steps wherein nucleic acid monomers are coupled to the support. Preferably, the drying follows at least about 75%, more preferably about 85%, and most preferably about 95% or more of the coupling steps.

Synthesis of Nucleic Acid Arrays

In the present invention, nucleic acid arrays can be prepared using a variety of synthesis techniques directed to high-density arrays of nucleic acids on solid supports. In brief, the methods can include light-directed methods, flow channel or spotting methods, pin-based methods, or combinations thereof For light-directed methods, see, for example, U.S. Pat. Nos. 5,143,854, 5,424,186 and 5,510,270. For techniques using mechanical methods, see PCT No. 92/10183, U.S. Pat. No. 5,384,261 and PCT/US99/00730. For a description of pin-based methods, see U.S. Pat. No. 5,288,514. A brief description of these methods is provided below. The methods of the present invention are equally amenable to the preparation of unimolecular double-stranded DNA arrays (see U.S. Pat. No. 5,556,752). In addition, the nucleic acid arrays prepared in the present methods will also include those arrays in which individual nucleic acids are interrupted by non-nucleotide portions (see, for example U.S. Pat. No. 5,556,752 in which probes such as polypeptides are held in a conformationally restricted manner by complementary nucleic acid fragments).

Various additional techniques for large scale polymer synthesis are known. Some examples include the U.S. Pat. Nos.: 5,143,854, 5,242,979, 5,252,743, 5,324,663, 5,384,261, 5,405,783, 5,412,087, 5,424,186, 5,445,934, 5,451,683, 5,482,867, 5,489,678, 5,491,074, 5,510,270, 5,527,681, 5,550,215, 5,571,639, 5,593,839, 5,599,695, 5,624,711, 5,631,734, 5,677,195, 5,744,101, 5,744,305, 5,753,788, 5,770,456, 5,831,070, and 5,856,011, all of which are incorporated by reference herein.

Light-directed Methods

For those embodiments using a single solid support, the nucleic acids of the present invention can be formed using techniques known to those skilled in the art of polymer synthesis on solid supports. Preferred methods include, for example, "light directed" methods which are one technique in a family of methods known as VLSIPS™ methods. The light directed methods discussed in U.S. Pat. No. 5,143,854 involve activating known regions of a substrate or solid support and then contacting the substrate with a preselected monomer solution. The known regions can be activated with a light source, typically shown through a mask (much in the manner of photolithography techniques used in integrated circuit fabrication). Other regions of the substrate remain inactive because they are blocked by the mask from illumination and remain chemically protected. Thus, a light pattern defines which regions of the substrate react with a given monomer. By repeatedly activating different sets of known regions and contacting different monomer solutions with the substrate, a diverse array of nucleic acids is produced on the substrate. Of course, other steps such as washing unreacted monomer solution from the substrate can be used as necessary.

The VLSIPS™ methods are preferred for the methods described herein. Additionally, the surface of a solid support, optionally modified with spacers having photolabile protecting groups such as NVOC and MeNPOC, is illuminated through a photolithographic mask, yielding reactive groups (typically hydroxyl groups) in the illuminated regions. A 3'-O-phosphoramidite activated deoxynucleoside (protected at the 5'-hydroxyl with a photolabile protecting group) is then presented to the surface and chemical coupling occurs at sites that were exposed to light. Following capping, and oxidation, the substrate is rinsed and the surface illuminated through a second mask, to expose additional hydroxyl groups for coupling, A second 5'-protected, 3'-O-phosphoramidite activated deoxynucleoside is presented to the surface. The selective photodeprotection and coupling cycles are repeated until the desired set of nucleic acids is produced Alternatively, an oligomer of from, for example, 4 to 30 nucleotides can be added to each of the known regions rather than synthesize each member in a monomer by monomer approach. Methods for light-directed synthesis of DNA arrays on glass substrates are also described in McGall el al., *J. Am. Chem. Soc.*, 119:5081–5090 (1997).

For the above light-directed methods wherein photolabile protecting groups and photolithography are used to create spatially addressable parallel chemical synthesis of a nucleic acid array (see also U.S. Pat. No. 5,527,681), computer tools may be used to assist in forming the arrays. For example, a computer system may be used to select nucleic acid or other polymer probes on the substrate, and design the layout of the array as described in, for example, U.S. Pat. No. 5,571,639.

Flow Channel or Spotting Methods

Additional methods applicable to library synthesis on a single substrate are described in U.S. Pat. No. 5,384,261 and in PCT/US99/00730. In the methods disclosed in this patent and PCT publication, reagents are delivered to the substrate by either (1) flowing within a channel defined on known regions or (2) "spotting" on known regions. However, other approaches, as well as combinations of spotting and flowing, may be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse nucleic acid sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed trough still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

The "spotting" methods of preparing nucleic acid libraries can be implemented in much the same manner as the flow channel methods. For example, a monomer A can be delivered to and coupled with a first group of reaction regions which have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire substrate surface can be sprayed or otherwise coated with a solution. In preferred embodiments, a dispenser moves from region to region, depositing only as much monomer as necessary at each stop. Typical dispensers include a micropipette to deliver the monomer solution to the substrate and a robotic system to control the position of the micropipette with respect to the substrate, or an ink=jet printer. In other embodiments, the dispenser includes a series of tubes, a manifold, an array of pipettes, or the like so that various reagents can be delivered to the reaction regions simultaneously. Still other spotting methods are described in PCT/US99/00730.

Pin-based Methods

Another method which is useful for the preparation of nucleic acid arrays and libraries involves "pin based synthesis." This method is described in detail in U.S. Pat. No. 5,288,514. The method utilizes a substrate having a plurality of pins or other extensions. The pins are each inserted simultaneously into individual reagent containers in a tray. In a common embodiment, an array of 96 pins/containers is utilized.

Each tray is filled with a particular reagent for coupling in a particular chemical reaction on an individual pin. Accordingly, the trays will often contain different reagents. Since the chemistry disclosed herein has been established such that a relatively similar set of reaction conditions may be utilized to perform each of the reactions, it becomes possible to conduct multiple chemical coupling steps simultaneously. In the first step of the process the invention provides for the use of substrate(s) on which the chemical coupling steps are conducted. The substrate is optionally provided with a spacer having active sites. In the particular case of nucleic acids, for example, the spacer may be selected from a wide variety of molecules which can be used in organic environments associated with synthesis as well as aqueous environments associated with binding studies. Examples of suitable spacers are polyethyleneglycols, dicarboxylic acids, polyamines and alkylenes, substituted with, for example, methoxy and ethoxy groups. Additionally, the spacers will have an active site on the distal end. The active sites are optionally protected initially by protecting groups. Among a wide variety of protecting groups which are useful are FMOC, BOC, t-butyl esters, t-butyl ethers, and the like. Various exemplary protecting groups are described in, for example, Atherton et al., SOLID PHASE PEPTIDE SYNTHESIS, IRL Press (1989). In some embodiments, the spacer may provide for a cleavable function by way of, for example, exposure to acid or base.

Solid Supports

Solid supports used in the present invention include any of a variety of fixed organizational support matrices. In some embodiments, the support is substantially planar. In some embodiments, the support may be physically separated into regions, for example, with trenches, grooves, wells and the like. Examples of supports include slides, beads and solid chips. Additionally, the solid supports may be, for example, biological, nonbiological, organic, inorganic, or a combination thereof, and may be in forms including particles, strands, gels, sheets, tubing, spheres, containers, capillaries, pads, slices, films, plates, and slides depending upon the intended use.

Supports having a surface to which arrays of nucleic acids are attached are also referred to herein as "biological chips". The support is preferably, silica or glass, and can have the thickness of a microscope slide or glass cover slip. Supports that are transparent to light are useful when the assay involves optical detection, as described, e.g., in U.S. Pat. No. 5,545,531. Other useful supports include Langmuir Blodgett film, germanium, (poly)tetrafluorethylene, polystyrene, (poly)vinylidenedifluoride, polycarbonate, gallium arsenide, gallium phosphide, silicon oxide, silicon nitride, and combinations thereof In one embodiment, the support is a flat glass or single crystal silica surface with relief features less than about 10 Angstoms.

The surfaces on the solid supports will usually, but not always, be composed of the same material as the substrate. Thus, the surface may comprise any number of materials, including polymers, plastics, resins, polysaccharides, silica or silica based materials, carbon, metals, inorganic glasses, membranes, or any of the above-listed substrate materials. Preferably, the surface will contain reactive groups, such as carboxyl, amino, and hydroxyl. In one embodiment, the surface is optically transparent and will have surface Si-OH functionalities such as are found on silica surfaces. In other embodiments, the surface will be coated with functionalized silicon compounds (see, for example, U.S. Pat. No. 5,919, 523).

Surface Density

The nucleic acid arrays described herein can have any number of nucleic acid sequences selected for different applications. Typically, there may be, for example, about 100 or more, or in some embodiments, more than $10^5$ or $10^8$. In one embodiment, the surface comprises at least 100 probe nucleic acids each preferably having a different sequence, each probe contained in an area of less than about 0.1 $cm^2$, or, for example, between about 1 /$mm^2$ and 1,000 /$mm^2$, and each probe nucleic acid having a defined sequence and location on the surface. In one embodiment, at least 1,000 different nucleic acids are provided on the surface, wherein each nucleic acid is contained within an area less than about $10^{-3}$ $cm^2$, as described, for example, in U.S. Pat. No. 5,510,270.

Arrays of nucleic acids for use in gene expression monitoring are described in PCT WO 97/10365, the disclosure of which is incorporated herein. In one embodiment, arrays of nucleic acid probes are immobilized on a surface, wherein the array comprises more than 100 different nucleic acids and wherein each different nucleic acid is localized in a predetermined area of the surface, and the density of the different nucleic acids is greater than about 60 different nucleic acids per 1 $cm^{2.}$ Arrays of nucleic acids immobilized on a surface which may be used also are described in detail in U.S. Pat. No. 5,744,305, the disclosure of which is incorporated herein. As disclosed therein, on a substrate, nucleic acids with different sequences are immobilized each in a known area on a surface. For example, 10, 50, 60, 100, $10^3$, $10^5$, $10^6$, $10^7$, or $10^8$ different monomer sequences may be provided on the substrate. The nucleic acids of a particular sequence are provided within a known region of a substrate, having a surface area, for example, of about 1 $cm^2$ to $10^{-10}$ $cm^2$. In some embodiments, the regions have areas of less than about $10^{-1}$, $10^{-2}$, $10^{-3}$, $10^{-4}$, $10^{-5}$, $10^{-6}$, $10^{-7}$, $10^{-8}$, $10^{-9}$, or $10^{-2}$. For example, in one embodiment, there is provided a planar, non-porous support having at least a first surface, and a plurality of different nucleic acids attached to the first surface at a density exceeding about 400 different nucleic acids/$cm^2$, wherein each of the different nucleic acids is attached to the surface of the solid support in a different known region, has a different determinable sequence, and is, for example, at least 4 nucleotides in length. The nucleic acids may be, for example, about 4 to 20 nucleotides in length. The number of different nucleic acids may be, for example, 1000 or more. In the embodiment where polynucleotides of a known chemical sequence are synthesized at known locations on a substrate, and binding of a complementary nucleotide is detected, and wherein a fluorescent label is detected, detection may be implemented by directing light to relatively small and precisely known locations on the substrate. For example, the substrate is placed in a microscope detection apparatus for identification of locations where binding takes place. The microscope detection apparatus includes a monochromatic or polychromatic light source for directing light at the substrate, means for detecting fluoresced light from the substrate, and means for determining a location of the fluoresced light The means for detecting light fluoresced on the substrate may in some embodiments include a photon counter. The means for determining a location of the fluoresced light may include an x/y translation table for the substrate. Translation of the substrate and data collection are recorded and managed by an appropriately programmed digital computer, as described in U.S. Pat. No. 5,510,270.

Applications Using Nucleic Acid Arrays

The methods and compositions described herein may be used in a range of applications including biomedical and genetic research as well as clinical diagnostics. Arrays of polymers such as nucleic acids may be screened for specific binding to a target, such as a complementary nucleotide, for example, in screening studies for determination of binding affinity and in diagnostic assays. In one embodiment, sequencing of polynucleotides can be conducted, as disclosed in U.S. Pat. No. 5,547,839. The nucleic acid arrays may be used in many other applications including detection of genetic diseases such as cystic fibrosis, diabetes, and acquired diseases such as cancer, as disclosed in U.S. patent application Ser. No. 08/143,312. Genetic mutations may be detected by sequencing by hydridization. In one embodiment, genetic markers may be sequenced and mapped using Type-IIs restriction endonucleases as disclosed in U.S. Pat. No. 5,710,000.

Other applications include chip based genotyping, species identification and phenotypic characterization, as described in U.S. patent application Ser. No. 08/797,812, filed Feb. 7, 1997, and U.S. application Ser. No. 08/629,031, filed Apr. 8, 1996. Still other applications are described in U.S. Pat. No. 5,800,992.

Gene expression may be monitored by hybridization of large numbers of mRNAs in parallel using high density arrays of nucleic acids in cells, such as in microorganisms such as yeast, as described in Lockhart et al., *Nature Biotechnology*, 14:1675–1680 (1996). Bacterial transcript imaging by hybridization of total RNA to nucleic acid arrays may be conducted as described in Saizieu et al., *Nature Biotechnology*, 16:45–48 (1998). Accessing genetic information using high density DNA arrays is further described in Chee, *Science* 274:610–614 (1996).

Still other methods for screening target molecules for specific binding to arrays of polymers, such as nucleic acids, immobilized on a solid substrate, are disclosed, for example, in U.S. Pat. No. 5,510,270. The fabrication of arrays of polymers, such as nucleic acids, on a solid substrate, and methods of use of the arrays in different assays, are also described in: U.S. Pat. Nos. 5,677,195, 5,624,711, 5,599,695, 5,445,934, 5,451,683, 5,424,186, 5,412,087, 5,405,783, 5,384,261, 5,252,743 and 5,143,854; PCT WO 92/10092; and U.S. application Ser. No. 08/388,321, filed Feb. 14, 1995.

Devices for concurrently processing multiple biological chip assays are useful for each of the applications described above (see, for example, U.S. Pat. No. 5,545,531). Methods and systems for detecting a labeled marker on a sample on a solid support, wherein the labeled material emits radiation at a wavelength that is different from the excitation wavelength, which radiation is collected by collection optics and imaged onto a detector which generates an image of the sample, are disclosed in U.S. Pat. No. 5,578,832. These methods permit a highly sensitive and resolved image to be obtained at high speed. Methods and apparatus for detection of fluorescently labeled materials are further described in U.S. Pat. Nos. 5,631,734 and 5,324,633.

Preferred Embodiments

In view of the technologies provided above, the present invention provides in one preferred embodiment, a method of preparing a nucleic acid array on a support, wherein each nucleic acid occupies a separate known region of the support and the nucleic acids are synthesized using the steps;

(a) activating a region of the support;

(b) attaching a nucleotide to a first region, the nucleotide having a masked reactive site linked to a protecting group;

(c) repeating steps (a) and (b) on other regions of the support whereby each of the other regions has bound thereto another nucleotide comprising a masked reactive site link to a protecting group, wherein the another nucleotide may be the same or different from that used in step (b);

(d) removing the protecting group from one of the nucleotides bound to one of the regions of the support to provide a region bearing a nucleotide having an unmasked reactive site;

(e) binding an additional nucleotide to the nucleotide with an unmasked reactive site;

(f) repeating steps (d) and (e) on regions of the support until a desired plurality of nucleic acids is synthesized, each nucleic acid occupying separate known regions of the support;

wherein some or all of the attaching and binding steps are followed by drying steps in which the support is exposed to a dry atmosphere for a period of time sufficient to reduce pitting on the array. Typically, the dry atmosphere is dry air (preferably dry filtered air), nitrogen or argon, or mixtures thereof, and the period of time is at least 30 seconds, although times of 45 seconds or one minute or more can also be used.

Preferably, the "activating" of step (a) is carried out using a channel block or photolithography technique, more preferably a photolithography technique. The "attaching" of step (b) is typically carried out using chemical means to provide a covalent bond between the nucleotide and a surface functional group present in the first region. In some embodiments, the surface functional group will be a group present on a nucleotide or nucleic acid that is already attached to the solid support. For example, nucleic acid arrays can be prepared using a solid support having a surface coated with poly-A nucleic acids to provide suitable spacing between the surface of the support and the nucleic acids that will be used in subsequent hybridization assays. Accordingly, the "attaching" can be, for example, by formation of a covalent bond between surface Si—OH groups and a group present on the first nucleotide of a nascent nucleic acid chain, or by formation of a covalent bond between groups present in a support-bound nucleic acid and a group present on the first nucleotide of a nascent nucleic acid. Typically, the groups present on nucleic acids which are used in covalent bond formation are the 3'- or 5-hydroxyl groups in the sugar portion or the molecule, or phosphate groups attached thereto.

The nucleotides used in this and other aspects of the present invention will typically be the naturally-occurring nucleotides, derived from, for example, adenosine, guanosine, uridine, cytidine and thymidine. In certain embodiments, however, nucleotide analogs or derivatives will be used (e.g., those nucleosides or nucleotides having protecting groups on either the base portion or sugar portion of the molecule, or having attached or incorporated labels, or isosteric replacements which result in monomers that behave in either a synthetic or physiological environment in a manner similar to the parent monomer). The nucleotides will typically have a protecting group which is linked to, and masks, a reactive group on the nucleotide. A variety of protecting groups are useful in the invention and can be selected depending on the synthesis techniques employed. For example, channel block methods can use acid- or base-cleavable protecting groups to mask a hydroxyl group in a nucleotide. After the nucleotide is attached to the support or growing nucleic acid, the protecting group can be removed by flowing an acid or base solution through an appropriate channel on the support.

Similarly, photolithography techniques can use photoremovable protecting groups. Some classes of photoremovable protecting groups include 6-nitroveratryl (NV), 6-nitropiperonyl (NP), methyl-6-nitroveratryl (MeNV), methyl6-nitropiperonyl (MeNP), and 1-pyrenylmethyl (PyR), which are used for protecting the carboxyl terminus of an amino acid or the hydroxyl group of a nucleotide, for example. 6-nitroveratryloxycarbonyl (NVOC), 6-nitropiperonyloxycarbonyl (NPOC), methyl-1-nitroveratryloxycarbonyl (MeNVOC), methyl-6-nitropiperonyloxycarbonyl (MeNPOC), 1-pyrenylmethyloxycarbonyl (PyROC), which are used to protect the amino terminus of an amino acid are also preferred. Clearly, many photosensitive protecting groups are suitable for use in the present invention (see, U.S. Pat. No. 5,489,678 and PCT WO 94/10128).

In addition, novel photoremovable protecting groups such as 5'-O-pyrenylmethyloxy carbonyl (PYMOC) and methylnitropiperonyloxycarbonyl (MeNPOC) have been described in the copending U.S. patent application Ser. No. 08/630,148, filed Apr. 10, 1996, the contents of which are hereby incorporated by reference.

In addition to the above-described protecting groups, the present invention employs protecting groups, such as the 5'-X-2'-deoxythymidine 2-cyanoethyl 3'-N,N-diisopropylphosphoramidites in various solvents. In these protecting groups, X may represent the following photolabile groups: ((α-methyl-2-nitropiperonyl)-oxy)carbonyl (MeNPOC), ((Phenacyl)-oxy)carbonyl (PAOC), O-(9-phenylxanthen-9-yl) (PIXYL), and ((2-methylene-9,10-anthraquinone)-oxy)carbonyl (MAQOC).

Various methods for generating protected monomers have been described by the U.S. Pat. No. 5,744,305, which is incorporated by reference. Detailed methods for using photoremovable protecting groups are described in the U.S. Pat. No. 5,424,186, which is also hereby incorporated by reference.

The removal rate of the protecting groups depends on the wavelength and intensity of the incident radiation, as well as the physical and chemical properties of the protecting group itself. Preferred protecting groups are removed at a faster rate and with a lower intensity of radiation. For example, at a given set of conditions, MeNVOC and MeNPOC are photolytically removed faster than their unsubstituted parent compounds, NVOC and NPOC, respectively.

In addition to the above-described references, photocleavable protecting groups and methods of using such photocleavable protecting groups for polymer synthesis have been described in the copending applications Ser. No. 08/630,148 (filed Apr. 10, 1996) and Ser. No. 08/812,005 (filed Mar. 5, 1997) which are incorporated by reference herein.

Step (c) provides that steps (a) and (b) can be repeated to attach nucleotides to other regions of the solid support.

One of skill in the art will appreciate that steps (a) and (b) can be repeated a number of times to produce a solid support having a layer of attached nucleotides. Preferably, each attached nucleotide is in a known position.

In subsequent steps (d), (e) and (f), the protecting group is removed from one of the nucleotides to reveal a reactive site on the nucleotide. Thereafter, an additional nucleotide (optionally having a masked reactive site attached to a protecting group) is attached to the support-bound nucleotide. As above, these steps can be repeated to selectively attach or bind an additional nucleotide to any of the support-bound nucleotides. Still further, the steps of deprotecting and attaching an additional nucleotide can be carried out on the newly added nucleotides to continue the synthesis of the nascent nucleic acid.

As noted above, the above steps are preferably carried out in combination with a drying step in which We solid support is exposed to a dry atmosphere for a period of at least about 30 seconds.

A variety of methods can be used for drying the support during array preparation. Typically, the array can simply be exposed to a suitable dry atmosphere (e.g., dry air, argon, nitrogen or other inert gases and combinations of gases) for a period of time which is sufficient to remove substantially all moisture from the array. The precise amount of time will be a function of the temperature of drying. At ambient temperatures, the drying time will preferably be about 30 seconds, 40 seconds, 50 seconds, one minute or more. One of skill in the art will understand that suitable drying can also be accomplished by passing a stream of dry air (or another dry gas) over the array, either at ambient temperature or with slight warning of either the array or the atmosphere. Accordingly, the times suitable for drying the array can be adjusted consistent with the environmental temperature at which drying occurs. Still firer, when a dry atmosphere is passed over the array, adequate drying can be monitored by measuring the amount of moisture in the effluent atmosphere.

Preferably, the array is dried following each step wherein a base is added to the developing nucleic acids. Alternatively, drying can be carried out following only a portion of the attaching and binding steps. In this manner, drying can be performed after every second step, every third step, every fourth step, or in a less regular approach.

In a further preferred embodiment, the array preparing comprises:
a) removing a photoremovable protecting group from at least a first area of a surface of a substrate, the substrate comprising immobilized nucleotides on the surface, and the nucleotides capped with a photoremovable protective group, without removing a photoremovable protecting group from at least a second area of the surface;
b) simultaneously contacting the first area and the second area of the surface with a first nucleotide to couple the first nucleotide to the immobilized nucleotides in the first area, and not in the second area, the first nucleotide capped with a photoremovable protective group;
c) removing a photoremovable protecting group from at least a part of the first area of the surface and at least a part of the second area;
d) simultaneously contacting the first area and the second area of the surface with a second nucleotide to couple the second nucleotide to the immobilized nucleotides in at least a part of the first area and at least a part of the second area;
e) performing additional removing and nucleotide contacting and coupling steps so that a matrix array of at least 100 nucleic acids having different sequences is formed on the support;
with the proviso that the coupling steps further comprise a drying step wherein the solid support is exposed to a dry atmosphere as described above.

In this embodiment of the invention, the steps of removing photoremovable protecting groups, coupling nucleotides to specific areas, removing protecting groups from the coupled nucleotides, and coupling additional nucleotides can all be carried out as described in, for example, U.S. Pat. No. 5,510,270, with the added feature that the coupling steps are followed with drying steps to remove substantially all of the solvent (typically water or aqueous mixtures) remaining on the developing array.

In still further preferred embodiments, the nucleoside phosphoramidite monomers used in the methods described above have the formula:

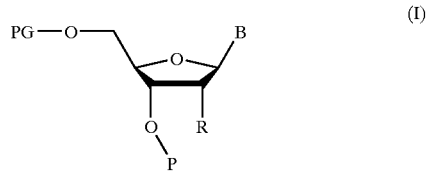

(I)

wherein B represents adenine, guanine, thymine, cytosine, uracil or analogs thereof; R is hydrogen, hydroxy, protected hydroxy, halogen or alkoxy; P is a phosphoramidite group; and PG is a photoremovable protected group.

In the group of embodiments using monomers of formula (I), B is preferably adenine, guanine, thymine, cytosine or uracil. More preferably, B is adenine, guanine, thymine, or cytosine, and R is hydrogen. Still more preferably, the array prepared using the monomers above comprises at least 10 different nucleic acids, more preferably at least 100 different nucleic acids, still more preferably at least 1000 different nucleic acids. Most preferably, the array comprises at least 10,000 to 100,000 or more different nucleic acids. Additionally, each different nucleic acid is in a region having an area of less than about 1 cm$^2$, more preferably less than about 1 mm$^2$.

In still other preferred embodiments, B is adenine, guanine, thymine, or cytosine; R is hydrogen; and the drying steps are performed by exposing the array to atmospheres of dry air, nitrogen, argon or mixtures thereof.

In further preferred embodiments, B is adenine, guanine, thymine, or cytosine; R is hydrogen; PG is MeNPOC and the drying atmosphere used is argon or dry air.

In still further preferred embodiments, B is adenine, guanine, thymine, or cytosine; R is hydrogen; PG is MeNPOC, P is —P(OCH$_2$CH$_2$CN)N(iPr)$_2$ and the drying atmosphere used is argon or dry air.

One of skill in the art will appreciate that the present invention can be readily modified to use protected nucleoside phospohoramidite monomers wherein the protecting group on the 5' hydroxy is acid or base removable. Such modifications will render the invention applicable to other synthesis methodologies such as flow channel and spotting methods described in more detail above. Regardless of the array synthesis methods, suitable drying of the array between synthesis steps can reduce pitting seen in the arrays and increase both the yield of arrays suitable for functional applications and the functional performance of the arrays themselves.

EXAMPLES

In the example below, nucleic acid probe arrays were prepared using photolithography and a silica wafer as the solid substrate. Preparation was typically on a 5 inch by 5 inch wafer which can be cut into 49 replicates of a probe array having about 400,000 distinct probe sequences, or 400 replicates of a probe array having about 50,000 distinct probe sequences. The density of the nucleic acid probes is about 1–10 picomoles per cm$^2$.

Example 1

To evaluate the source of "pitting" seen on some chips from the 49-chip wafers, various mechanisms (e.g., physical defects in the substrates due to abrasions, residues, etc.) were considered and eliminated as likely causes. Pitting was found to be a probe synthesis phenomenon occurring during the chemical addition steps. Test vehicles were devised and image analysis software was developed to characterize the extent and severity of pitting on whole wafers.

Test vehicle A: This vehicle was a nucleic acid array constructed using a full 74-step synthesis in which the wafer was held in a vertical orientation with one corner pointing downward. Areas of the array were illuminated through a mask and reagents were presented to the areas through an attached flow cell.

Test vehicle B: This vehicle was a nucleic acid array constructed using 20step synthesis of probes. Areas of the array were illuminated through a checkerboard of open-reticle mask.

Test vehicle C: This vehicle was a nucleic acid array using a 20-step synthesis procedure in an enclosed (backside) photolysis setup. This vehicle was the most rapid and eliminated the environmental variables for certain experiments.

Figure 3:
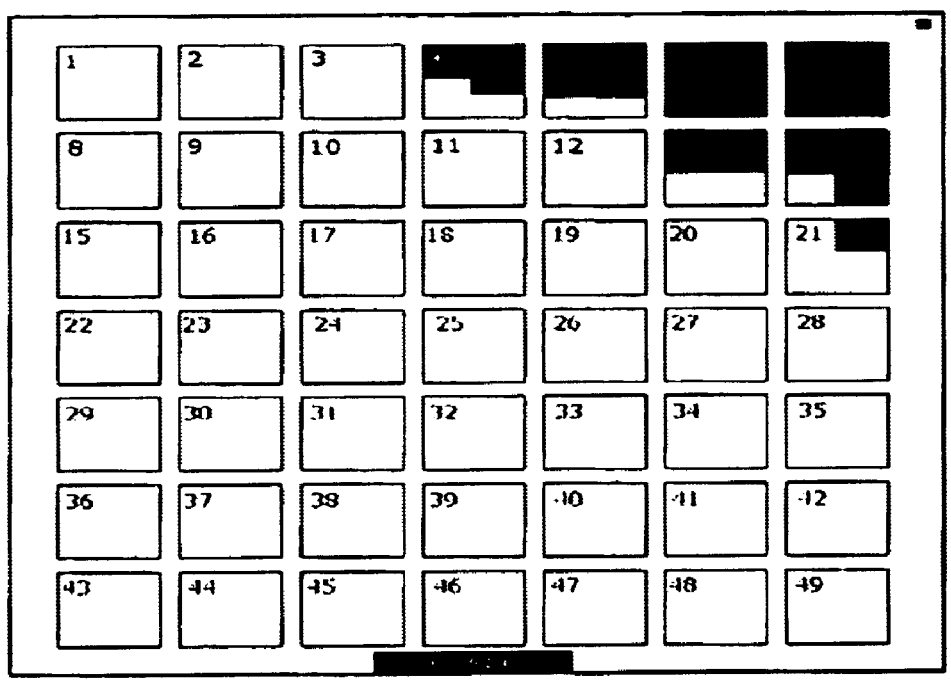
FIG. 3 shows a wafer map with chips 1–9 numbered and the pitted region mapped to the #7 corner.
Figure 4:
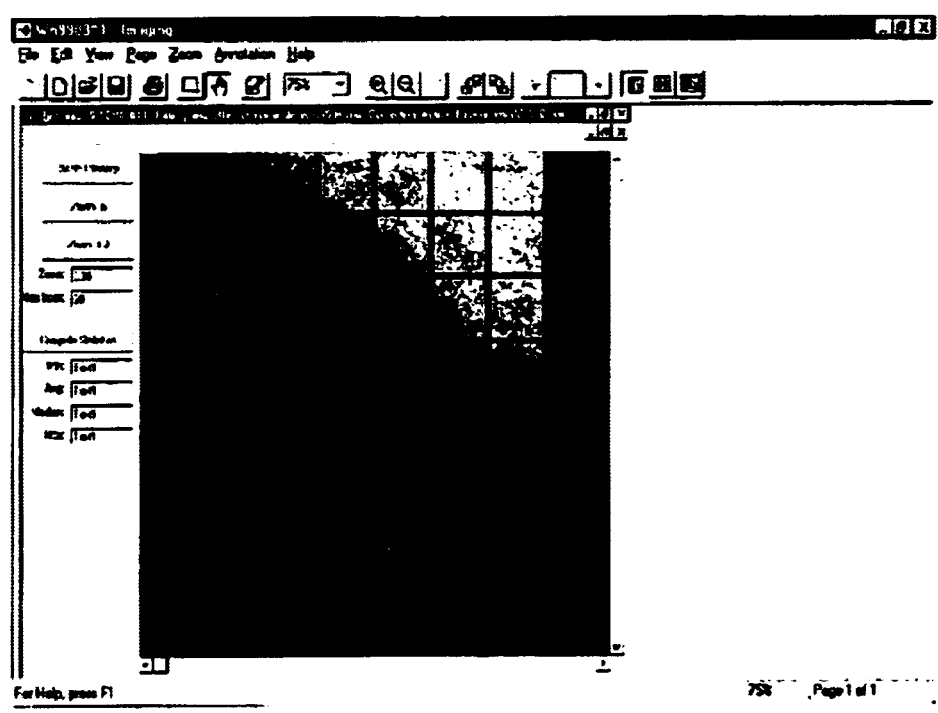
FIG. 4 shows pit mapping by a Pit Analysis Program for a 49-chip wafer. Pitting can be seen over one-third of the wafer, corresponding to the corner of the wafer held in the bottom position (the wafer is held vertical during synthesis with one corner downward).

Following construction of the test vehicles, mosaic images from the wafers were obtained using a SYBR green test method. For vehicles A and B, pitting was concentrated in the corner chip (#7, corner oriented to the bottom during chemical addition steps). Under typical conditions, pitting was observed to cover the bottom one-third of the wafer (see FIGS. 3 and 4).

Figure 5:
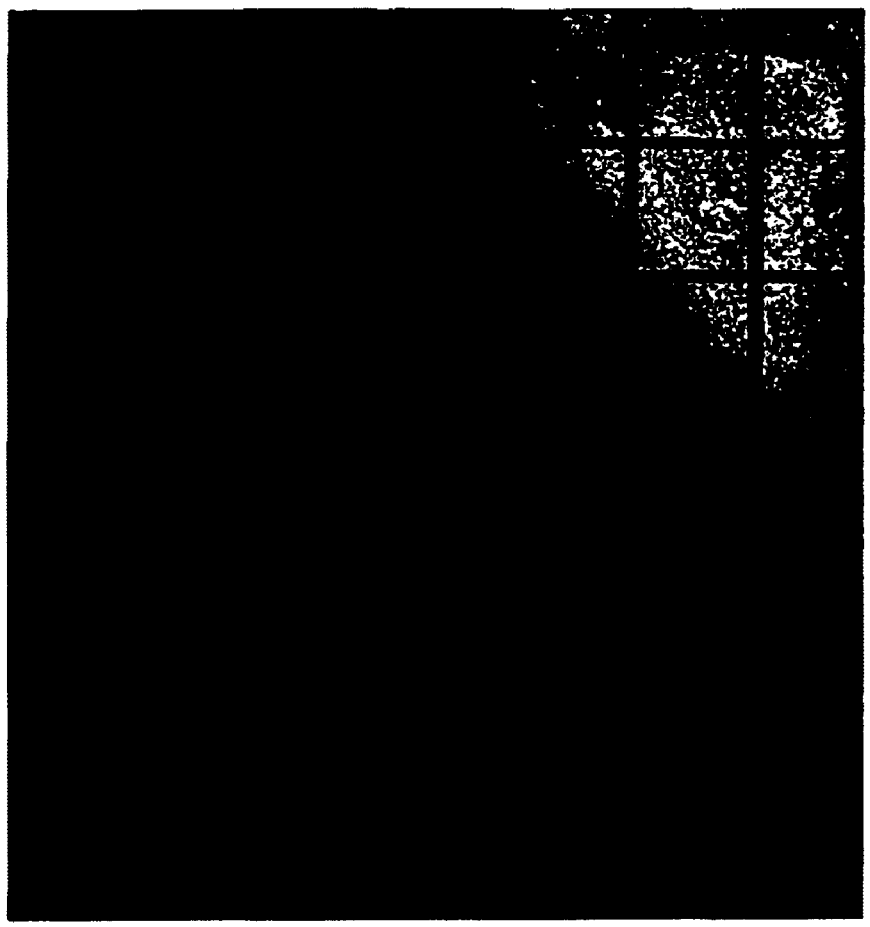
FIG. 5 shows pitting on the #7 corner when standard wafer loading (synthesis) is used (corner #7 downward).
Figure 6:
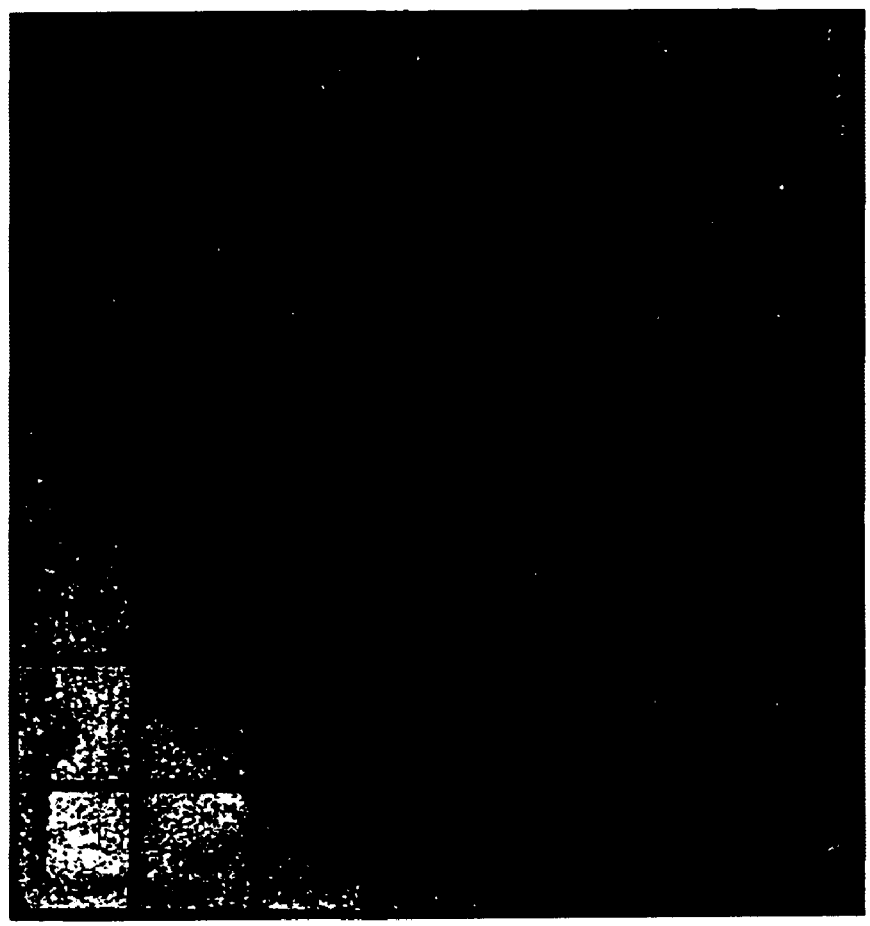
FIG. 6 shows pitting on the #43 corner of the wafer when the wafer is loaded 180° from standard loading (#43 corner is positioned at the bottom of the flowcell).

Wafer rotation experiments indicated that pitting consistently occurred on the corner of the wafer oriented towards the bottom of the flow cell. As shown in FIGS. 5 and 6, pitting occurred in corner #7 with standard loading (FIG. 5) and in corner #43 when the wafer is loaded 180° from the standard loading FIG. 6 wherein #43 is at the bottom of the loading flowcell).

When preparation of Test Vehicle A was aborted, and the partially prepared wafers were evaluated using the SYBR-Green staining method, wafers which were aborted early did not exhibit as much pitting as those which were aborted towards the end of the 74-step synthesis cycle. This indicated that pitting defects were from a cumulative process and were not due to a single pre- or post-synthesis process step.

Figure 7:
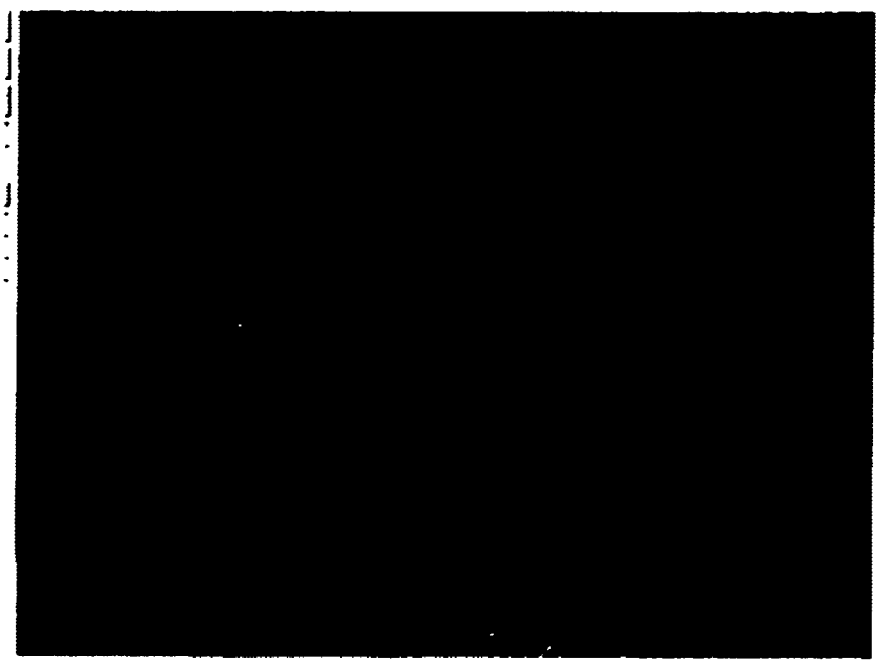
FIG. 7 shows a pit map from an array prepared using backside photolysis. Essentially no pitting is observed when the array is not exposed to the environment.

The cause of pitting was further investigated with Test Vehicles B and C. Test Vehicle B was constructed using additional filters for the synthesis reagents and the argon atmosphere. The filters were selected to remove potential interfering particulate matter (0.5 micron filter for the reagents and 0.003 micron filter for the argon). However, wafers synthesized with reagent and argon filtering continued to show substantial pitting. Using an enclosed, backside photolysis method Test Vehicle C was constructed and wafers synthesized did not show pitting (see FIG. 7).

Additional experiments indicated that the mechanism of pitting was not due to abrasion from airborne particles being dragged over the wafer surface during reagent addition.

Figure 8:
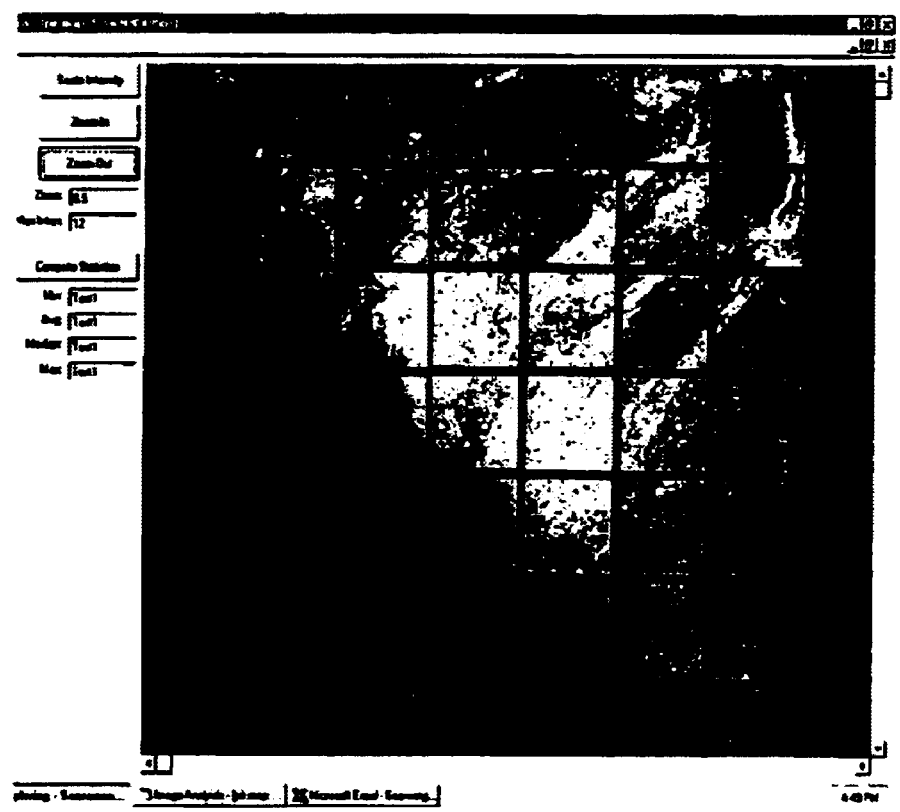
FIGS. 8–10 show the pit maps from wafers prepared in the standard orientation but using varied drying times between synthesis steps.
Figure 9:
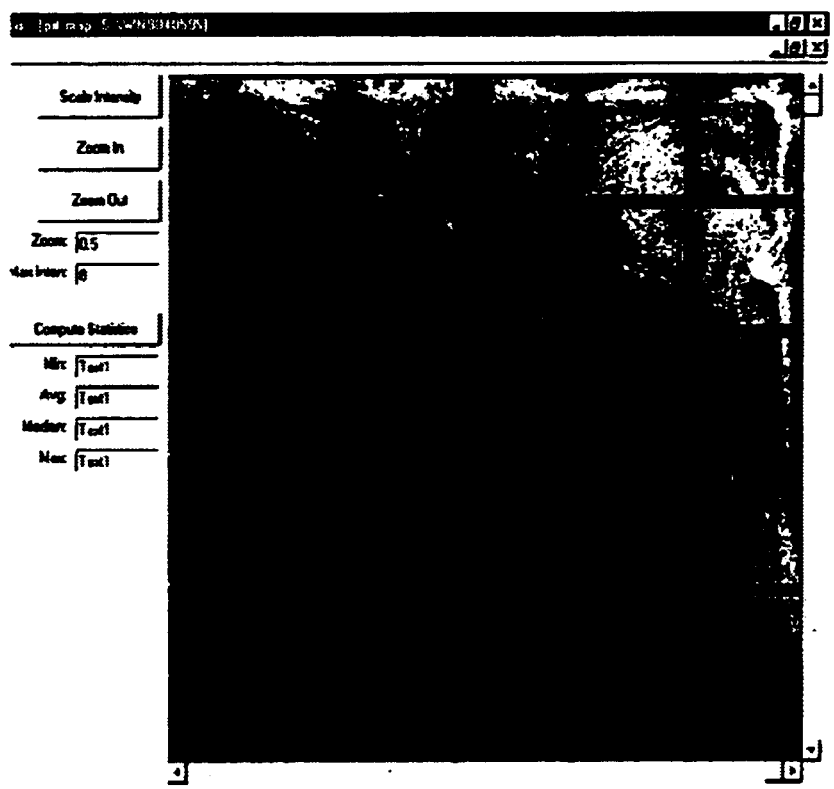
Figure 10:
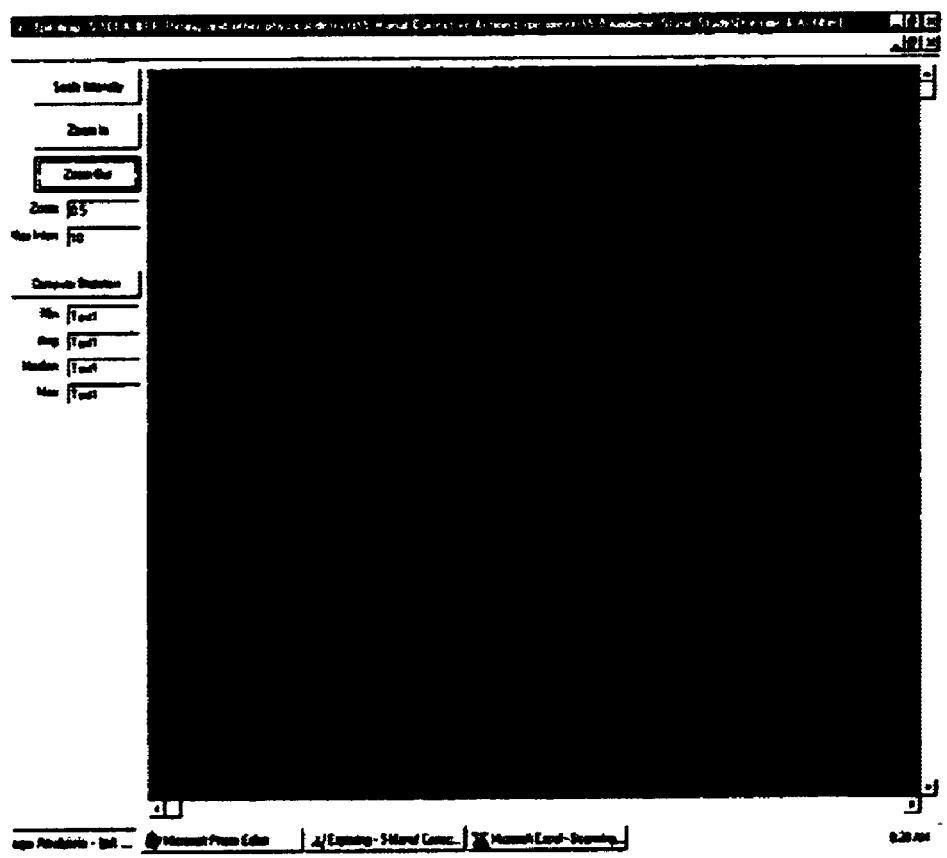

Another possibility was that an airborne contaminant adhered to the surface of the wafer during synthesis, blocked the growth of probes and possibly detached at a later point in synthesis. This mechanism of pitting could potentially be due to excess liquid solvent on the wafer which attracts airborne particulates and promotes their adhesion to the wafer. To evaluate this possibility, wafers were synthesized with varying drying times following each nucleic acid addition step. FIGS. 8–10 illustrate the pitting which occurs on wafers following a 10-sec drying time during flow cell synthesis (FIG. 8), a 25-sec drying time (standard method, FIG. 9), and a 75-sec drying time (FIG. 10). As can be seen from FIG. 10, wafers given the longer 75-sec drying time showed no significant pitting. Additional experiments with various intermediate drying times showed that the extent and severity of pitting increased with decreasing argon drying times.

To confirm the observation above, a set of Product Murine 11K confirmation runs were carried out using 75 second drying times. To verify that the increased drying time would not negatively impact the functional performance of the arrays, assays were performed with complex target samples. Arrays prepared with standard drying times of 25 seconds and the longer 75 second drying times were prepared and tested with labeled cRNA target which was prepared from a Murine B-cell cDNA library. The target was spiked with 1.5 pM each of bio B, dap, lys, phe, thr, and trp, 5 pM bio C, 25 pM bio D and 100 pM cre labeled control transcripts. The results showed that all functional tests for the arrays manufactured with 75 second drying times were equivalent to control arrays, with the exception that arrays from the #7 corner of the control wafer showed significant pitting while those made with the extra drying time showed no pitting.

Additional evaluation of synthesis/drying methods indicated that as little as 15–20 seconds of additional drying time (40–45 seconds total) was sufficient to reduce pitting to an insignificant level.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entire for all purposes.

What is claimed is:

1. A method of reducing pitting of a solid support in the preparation of a nucleic acid array on said solid support, wherein said solid support is non-porous and substantially planar or comprises substantially planar regions, said method comprising:

a) attaching a plurality of nucleic acids to said support to form an array; and b) drying said array by exposing to a dry atmosphere for a period of at least 30 seconds.

2. A method in accordance with claim 1, wherein said attaching comprises a stepwise coupling of nucleic acid monomers to a nucleic acid probe array wherein each of said probes are from 5 to 50 monomers in length and said drying comprises following at least a portion of said stepwise coupling steps with a step of exposing the array to a dry atmosphere for a period of at least 50 seconds.

3. A method in accordance with claim 2, wherein said portion is at least about 70% of said coupling steps.

4. A method in accordance with claim 2, wherein said portion is at least abut 85% of said coupling steps.

5. A method in accordance with claim 2, wherein said portion is at least about 95% of said coupling steps.

6. A method accordance with claim 1, wherein each nucleic acid occupies a separate known region of the support, said attaching step (a) further comprises:

(i) activating a region of the support;

(ii) attaching a nucleotide to a first region, said nucleotide having a masked reactive site liked to a protecting group;

(iii) repeatng steps (i) and (ii) on other regions of said support whereby each of said other regions has bound thereto another nucleotide comprising a masked reactive site link to a protecting group, wherein said another nucleotide may be the same or different from that used in step (ii);

(iv) removing the protecting group from one of the nucleotides bound to one of the regions of the support to provide a region bearing a nucleotide having an unmasked reactive site;

(v) binding an additional nucleotide to the nucleotide with an unmasked reactive site;

(vi) repeating steps (iv) and (v) on regions of the support until a desired plurality of nucleic acids is synthesized, each nucleic acid occupying separate known regions of the support;

wherein at least a portion of said attaching and said binding steps are followed by drying steps wherein said solid support is exposed to a dry atmosphere for a period of at least 50 seconds.

7. A method in accordance with claim 1, wherein said attaching step (a) comprises the sequential steps of:

(i) removing a photoremovable protecting group from at least a first area of a surface of a substrate, said surface comprising immobilized nucleotides on said surface, said nucleotides with a photoremovable protective group, without removing a photoremovable protecting group from at least a second area of said surface;

(ii) simultaneously contacting said first area and said second area of said surface with a first nucleotide to couple said first nucleotide to said immobilized nucleotides in said first area, and not in said second area, said first nucleotide capped with said photoremovable protective group;

(iii) removing a photoremovable protecting group from at least a part of said first area of said surface and at least a part of said second area;

(iv) simultaneously contacting said first area and said second area of said surface with a second nucleotide to couple said second nucleotide to said immobilized nucleotides in at least a part of said first area at least a part of said area;

(v) performing additional irradiating and nucleotide contacting and coupling steps so that a matrix array of at least 100 nucleic acids having different sequences is formed on said support;

wherein at least a portion of said contacting steps are followed by drying steps wherein said solid support is exposed to a dry atmosphere selected from the group consisting of dry air, nitrogen, argon and mixtures thereof for a period of at least 50 seconds.

8. A method in accordance with claim 7, wherein said portion is at least about 70% of said contacting steps.

9. A method in with claim 7, wherein said portion is at least about 85% of said contacting steps.

10. A method in accordance with claim 7, wherein said portion is at least about 95% of said contacting steps.

11. A method in accordance with claim 9, wherein said array comprises at least 10 different nucleic acids.

12. A method in accordance with claim 9, wherein said array comprises at least 100 different nucleic acids.

13. A method in accordance with claim 9, wherein said array at least 1000 different nucleic acids.

14. A method in accordance with claim 9, wherein said array comprises at least 10,000 different nucleic acids.

15. A method in accordance with claim 9, wherein said array comprises at least 100,000 different nucleic acids.

16. A method in accordance with claim 9, wherein each different nucleic acid is in a region having an area of less than about 1 $cm^2$.

17. A method in accordance with claim 9, wherein each different nucleic acid is in a region having an area of less than about 1 $mm^2$.

* * * * *

UNITED STATES PATENT AND TRADEMARK OFFICE
CERTIFICATE OF CORRECTION

PATENT NO.   : 6,806,361 B1
DATED        : October 19, 2004
INVENTOR(S)  : Kajisa et al.

It is certified that error appears in the above-identified patent and that said Letters Patent is hereby corrected as shown below:

Column 17,
Line 14, insert -- prepare -- after "to.".
Line 23, replace "abut" with -- about. --.
Line 31, replace "liked" with -- linked. --.
Line 33, replace "repeatng" with -- repeating. --.

Column 18,
Line 6, insert -- capped -- after "nucleotides.".
Line 33, insert -- accordance -- after "in.".

Signed and Sealed this

Seventh Day of February, 2006

JON W. DUDAS
*Director of the United States Patent and Trademark Office*